United States Patent [19]
Goltra

[11] Patent Number: 5,794,208
[45] Date of Patent: Aug. 11, 1998

[54] CREATING AND USING PROTOCOLS TO CREATE AND REVIEW A PATIENT CHART

[76] Inventor: Peter S. Goltra, 22717 Goltra La., Middleburg, Va. 22117

[21] Appl. No.: 609,828

[22] Filed: Mar. 1, 1996

[51] Int. Cl.$^6$ .......................... G06F 159/00; G06F 17/24
[52] U.S. Cl. .......................... 705/3; 705/1; 705/2; 705/4; 707/530; 707/531
[58] Field of Search .......................... 705/2, 1, 3, 4; 283/54, 900, 115; 345/333, 334, 336, 338; 434/430; 707/530, 531, 539, 540

[56] References Cited

U.S. PATENT DOCUMENTS

| | | | |
|---|---|---|---|
| 4,839,822 | 6/1989 | Dormond et al. | 128/924 |
| 5,089,978 | 2/1992 | Lipner et al. | 364/555.01 |
| 5,262,943 | 11/1993 | Thibado et al. | 340/722 |
| 5,265,010 | 11/1993 | Evans-Paganelli et al. | |
| 5,387,164 | 2/1995 | Brown, Jr. | 482/9 |

*Primary Examiner*—Frantzy Poinvil
*Attorney, Agent, or Firm*—Burns, Doane, Swecker and Mathis, L.L.P.

[57] ABSTRACT

A method and apparatus for creating and using a reusable medical protocol to create a patient chart is provided. The protocol is created by selecting various medical findings from a database containing a plurality of coded medical findings, wherein the coded medical findings are grouped into several different sections such as a symptoms section, a history section, a physical findings section, a diagnoses section, a test section and a therapy section. Once the medical findings have been selected, the order of the display of the findings within the protocol is selected. The created protocol is then displayed on a display screen. The healthcare professional then selects medical findings displayed in the protocol which describe the patient's situation. According to the present, the selected medical findings are automatically placed in the correct section of the patient chart based upon the code of the selected medical finding, wherein the patient chart is divided into the same sections as the protocol.

22 Claims, 3 Drawing Sheets

| | | |
|---|---|---|
| PROTOCOL NAME | <ANGINA                                    > | |
| DESCRIPTION | <SCREENING FOR CHEST PAIN                  > | |
| 1 | -------- | |
| 2 | SYMPTOMS | |
| 3 | -------- | |
| 4 | +CHEST PAIN OCCURRENCE | SYM |
| 5 | +CHEST PAIN STARTING WITH | SYM |
| 6 | +CHEST PAIN RELIEVED BY | SYM |
| 7 | +PALPITATIONS | SYM |
| 8 | +DIFFICULTY BREATHING (DYSPNEA) | SYM |
| 9 | AWAKENING AT NIGHT SHORT OF BREATH (PND) | SYM |
| 10 | ANKLE SWELLING WITHOUT AN INJURY (EDEMA - AS A SYMPTOM) | SYM |
| 11 | +DIZZINESS | SYM |
| 12 | -------- | |
| 13 | HISTORY | |
| 14 | -------- | |
| 15 | +SMOKING CIGARETTES | HIS |
| 16 | BEING SEDENTARY | HIS |
| 17 | MODERATE EXERCISING 3 OR MORE TIMES A WEEK | HIS |
| 18 | PHYSICAL ACTIVITY TOLERANCE RECENTLY DECREASED | HIS |
| 19 | A RECENT ECG WAS ABNORMAL | HIS |
| 20 | A RECENT CHOLESTEROL LEVEL WAS HIGH | HIS |
| 21 | CURRENT MEDICATION SEEMS TO BE HELPING | HIS |
| 22 | FEEL CURRENT MEDICATION IS CAUSING A PROBLEM | HIS |
| 23 | +STOPPED TAKING CURRENT MEDICATION | HIS |
| 24 | RAN OUT OF CURRENT MEDICATION | HIS |
| 25 | +RECENT EPISODE (S) OF ANGINA | HIS |
| 26 | ANGINA OCCURRING MORE FREQUENTLY OR WITH MORE SEVERITY | HIS |
| 27 | -------- | |
| 28 | PHYSICAL EXAM | |
| 29 | -------- | |
| 30 | PROTOCOL: VITAL SIGNS | |
| 31 | +BRADYCARDIA | PHY |
| 32 | +TACHYCARDIA | PHY |
| 33 | +COMBINED SYSTOLIC AND DIASTOLIC HYPERTENSION | PHY |
| 34 | HYPOTENSION | PHY |
| 35 | +HEART SOUNDS | PHY |
| 36 | +MURMUR | PHY |
| 37 | +EDEMA | PHY |
| 38 | -------- | |
| 39 | DIAGNOSES | |
| 40 | -------- | |
| 41 H | +DIABETES MELLITUS | DIS |
| 42 H | +HYPERTENSION | DIS |
| 43 | -------- | |
| 44 | THERAPY | |
| 45 | -------- | |
| 46 | ASPIRIN 325 MILLIGRAM TAB 2 PO Q4H PRN DSP:100 BRAND: REGULAR STR | RX |
| 47 | +ANGINAL PREPARATIONS | RX |
| 48 | +BETA ADRENERGIC BLOCKING AGENTS | RX |
| 49 | +CALCIUM CHANNEL BLOCKERS | RX |

FIG. 3

CREATING AND USING PROTOCOLS TO CREATE AND REVIEW A PATIENT CHART

FIELD OF THE INVENTION

The present invention relates to a method and apparatus for creating patient charts by healthcare professionals, and more particularly to a method and apparatus for creating and using medical protocols to create and review patient charts.

BACKGROUND OF THE INVENTION

While many aspects of the operation and administration at hospitals and other healthcare facilities have been computerized over the past years, one of the most important aspects, the generation of patient charts, the updating of these charts, the review of the chart, and the generation of care plans by healthcare professionals such as doctors, nurses, therapists, and the like, is still performed largely by hand. As a result, while a patient chart of some type is normally generated shortly after a patient is admitted to the healthcare facility for a particular service, for example, an intensive care unit, cardiac surgery unit, or the like, the chart may not always be updated to reflect actual progress by the patient.

When a patient comes into a health care facility, the patient may have numerous related or unrelated problems that the healthcare provider will have to sort through when determining what is wrong with the patient and what treatments should be prescribed for the patient. Manually reviewing the chart for previous clinical findings relevant to the current problems can be a very time consuming and errorprone procedure. The diagnostic step in the treatment of the patient can thus be a very difficult process and arguably the most important step in treating a patient. Today, most healthcare professionals must rely on their memory and experience as well as written materials when making a diagnosis. Unfortunately, all of the needed materials may not be available during the examination of the patient and thus important questions may not be asked or tests performed which could help the healthcare professional in determining the correct diagnosis for the problems being experienced by the patient. Thus, it would be advantageous to allow healthcare professionals to create medical protocols which prompt the healthcare professional with lists of questions that should be asked, symptoms to look for, and tests that should be run, during the examination process.

Even after a diagnosis has been made and a care plan has been devised, the patient chart may not be referred to when the healthcare professional is preparing progress notes on the patient. Thus, there is no check to assure that the original treatments have in fact been followed, or that proposed resolution dates in the chart have been met or updated. When changes in the chart are made as a result of changes in the status of a patient, such changes are frequently not entered in the original chart. Thus, good archival records are not generally maintained for changes in treatment. The professional notes for a particular patient frequently do not include an updated version of the patient's chart. Further, even though a form may be available for progress notes, the form does not take into account the unique problems of the individual patient, and does not give the healthcare professional a checklist of items to be investigated for such problems or suggested interventions or resolution dates for the particular patient problem. When changes are made or expected outcomes are not achieved, the reasons for such occurrences are seldom provided, making any further review far more difficult. Again, a good archival record of what has been done for the particular patient is not readily available.

Because of the absence of good archival records, and the absence of reasons for changes or deviations, tracking a problem for quality control, legal or other reasons is difficult, and it is difficult to research the relative effectiveness of various interventions or to perform other research from the records.

The lack of a complete archival record can also cause significant problems for healthcare professionals who must adequately document the examination and treatment of patients whose medical bills are being paid by insurance companies. If the healthcare professional does not provide proper documentation, the insurance companies will not pay the bills. Furthermore, healthcare professionals have less time to spend with each patient these days. As a result, the healthcare professional does not have time to determine from the original chart and the added progress notes, if they are available, the previous problems of the patient and what treatments were prescribed. Thus, the healthcare professional needs to have an easy way to review charts for each patient.

Even with computer based patient chart and/or progress note systems, many of the problems indicated above still exist. Such systems also in many instances lack flexibility so as to be configurable by the healthcare professional so as to provide specific help in determining diagnoses and for prompting the healthcare professional with lists of symptoms, questions which should be asked and tests that should be performed in certain circumstances. In addition, they frequently do not give the healthcare professional the ability to add special instructions or to add items as required. Further, it is generally not possible to obtain either an updated chart or historical chart upon request. Thus, there is a need for a computer based medical system which enhances the diagnostic capabilities of a healthcare provider, provides initial patient charts as well as updated or historical care plans.

SUMMARY OF THE INVENTION

In a patient encounter a physician/healthcare professional will typically ask the patient a series of questions. If the patient has had previous encounters, the healthcare professional will want to review the previous charts for the patient before the next encounter. Next, the healthcare professional will examine the patient, make an assessment of any problems which may be present, and perhaps order a series of tests to confirm the diagnosis. If a computer-based chart is to be used, a mechanism to facilitate the entry of the information is important. It is an object of the present invention to provide such a mechanism which is easy to create and flexible to use.

According to one embodiment of the present invention, a method and apparatus for creating and using a reusable medical protocol to create a patient chart is disclosed. The protocol is created by selecting various medical findings from a database containing a plurality of coded medical findings, wherein the coded medical findings are grouped into several different sections such as a symptoms section, a history section, a physical findings section, a diagnoses section, a test section and a therapy section. Once the medical findings have been selected, the order of the display of the findings within the protocol is selected. The created protocol is then displayed on a display screen. The healthcare professional then selects medical findings displayed in the protocol which describe the patient's situation. According to the present application, the selected medical findings are automatically placed in the correct section of the patient chart based upon the code of the selected medical finding, wherein the patient chart is divided into the same sections as the protocol.

BRIEF DESCRIPTION OF THE DRAWING FIGURES

These and other features and advantages of the invention will be readily apparent to one of ordinary skill in the art from the following written description, used in conjunction with the drawings, in which:

FIG. 3 illustrates an example of a protocol constructed according to one embodiment of the present invention.

DESCRIPTION OF THE PREFERRED EMBODIMENTS

Figure 1:
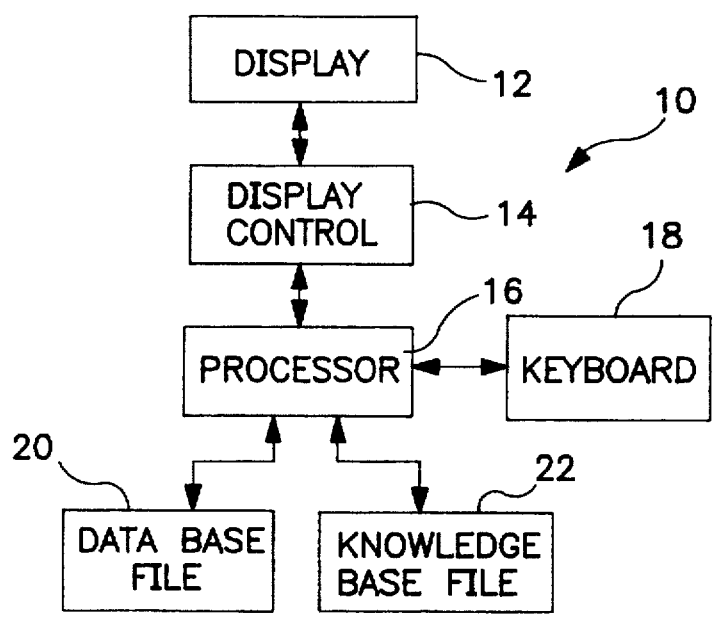
FIG. 1 illustrates a block diagram of a computer-based medical system according to one embodiment of the present invention.

The present invention uses a computer based medical system to allow a healthcare professional to chart the progress of a particular patient. A block diagram of the computer based medical system suitable for use in practicing the teachings of the present invention is illustrated in FIG. 1. The medical system 10 contains a processor 16 with one or more input devices such as a keyboard 18. The processor 16 also has a database file or memory 20 and a knowledge base file or memory 22. The processor 16 operates a standard display controller 14 which in turn, controls a display device 12 at the work station. The display device 12 can be any standard type of display monitor, attached or wireless. Furthermore, the apparatus 10 can be networked to other such medical systems not illustrated which can be placed around a hospital or healthcare facility. This allows multiple people to use the medical system for the same or for multiple patients.

The present invention is based upon on medical findings. Medical findings are defined as symptoms, history, physical findings, diagnoses, tests, and therapy which may be present for a particular patient. The database file 20 contains over 50,000 such medical findings which are divided into categories such as symptoms, history, physical findings, diagnoses, tests, and therapy. Furthermore, the descriptions of the medical findings stored in the database file 20 are hierarchical and can have up to eight levels of description. The first level gives the simplest explanation of a medical finding, for example, a cough. The explanations become more detailed the lower the level. As noted above, a first level finding may be a cough, while a second level finding may be a brassy cough. Another feature of the database memory 20 is that all of the medical findings are coded so as to be distinct from each other. For example, each medical finding can be assigned an internal number which uniquely identifies that particular medical finding. In addition, each medical finding also contains a code which indicates which category within the database file 20 the medical finding is associated with. For example, a medical finding may contain the code SYM to indicate that the medical finding is associated with the symptom section; HIS to indicate that the medical finding is associated with the history section; PHY to indicate that the medical finding is associated with the physical section; DIS to indicate that the medical finding is associated with the diagnoses section; TST to indicate that the medical finding is associated with the test section; and RX to indicate that the medical finding is associated with the therapy section.

As noted above, the medical system 10 also contains a knowledge base file 22. The knowledge base file contains a detailed description of over 2,000 diagnoses. The detailed description of the diagnoses uses the medical finding terms which are stored in the database file 20. For each diagnosis, each medical finding associated with the diagnosis is assigned a numerical value depending on how important such a medical finding may be to the diagnosis. For example, in the detailed description of the diagnosis for coronary artery stenosis, medical findings such as chest pain or discomfort and dyspnea (shortness of breath), which are strong showings of coronary artery stenosis, will be given high values while a lack of a desire for food may not be described in the diagnoses at all or given a very low value. In one embodiment of the present invention, medical findings are assigned values between 1 and 20 wherein the value 20 indicates the most important medical finding, however the invention is not limited thereto. Thus, the values assigned to each medical finding within the detailed description are proportional to how important such a medical finding is to the diagnosis. Furthermore, the values can vary for a given medical finding depending on a plurality of factors such as age of the patient and timeframe, i.e., when a symptom occurred in relation to other symptoms. For example, a white blood cell count of 18,000 may be given a high value if the patient is an adult while the same medical finding is not given a value at all if the patient is a new-born child because this is normal for a new-born child.

Here again, the medical findings used in the detailed descriptions of the diagnoses are all coded. In addition, over 400,000 links are provided between the database file 20 and the knowledge base file 22. In other words, the findings in the database file 20 occur over 400,000 times in the knowledge base file 22.

The detailed description of the diagnoses stored in the knowledge base file 22 contains lists of symptoms as well as personal and family history and physical findings which a patient should or may have experienced. In addition, the detailed diagnoses contain lists of tests, possible therapies, and medications which should be prescribed for the patient if the healthcare professional decides that the patient is experiencing a particular illness or problem.

According to one embodiment of the present invention, a method and apparatus for creating and using reusable medical protocols to create patient charts is disclosed. The clinical protocols are a structured combination of coded medical phrases selected from a structured medical database of coded phrases and are presented in the order of appearance selected by the healthcare professional. The healthcare professional can create a patient chart by selecting the desired phrases from the clinical protocol reflecting the responses from the patient to his/her questions or results from his/her examination, assessment, or other pertinent information the healthcare professional wishes to enter. Since the phrases are coded, upon selection of the phrases from the clinical protocol, the entered information is automatically structured in the chart in the same format as the format used in the medical database used to build the protocols. That is, symptoms automatically go into the symptoms section, physical findings into the physical examination section, diagnosis into the assessment section, etc. Since the healthcare professional who builds the clinical protocols can put in any combination of coded medical finding phrases, the protocols have a wide variety of uses. They can be used for routine examinations. They can also be used for a specific problem, such as the flu or angina. They can also be used for specific situations where a specified set of questions must always be asked or where certain information needs to be passed along to the patient. By using the protocol, nothing will be forgotten, since all the questions and the information are prompted each time the protocol is used.

The clinical protocols can be stored and used again when the patient returns either for entry of new visit information or equally important, as a mechanism to review the chart. In the latter use, the patient's chart is matched against the protocol. Since all the findings are coded, a healthcare professional can quickly see which findings in the chart are present that match the medical findings in the protocol. For example, after several visits to the healthcare professional for various problems, the patient's chart may contain hundreds or thousands of medical findings. When the patient returns complaining of a previous problem, the healthcare professional can select the matching option so as to compare the findings in a protocol for the possible problem with the medical findings in the patients chart.

Figure 2:
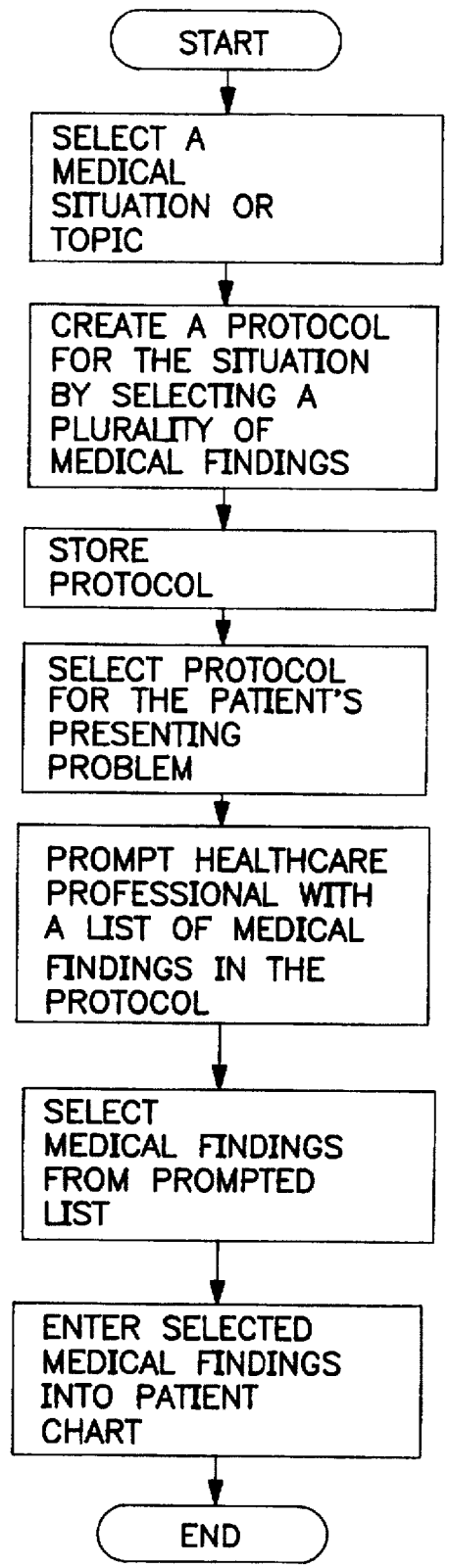
FIG. 2 illustrates a flowchart according to the operation of one embodiment of the present invention.

The creation and use of the protocols will now be described in more detail with regard to FIG. 2. First of all, the healthcare professional selects a topic or situation for which the healthcare professional wishes to create a reusable protocol. The healthcare professional then structures the protocol by entering medical findings into the protocol which are associated with the topic of the protocol. The healthcare professional can also be prompted with lists of associated medical findings by selecting an intelligent prompting mechanism. Intelligent prompting is more fully disclosed in U.S. patent application Ser. No. 08/609,689 entitled "Intelligent Prompting," now pending which is being filed concurrently herewith and is expressly incorporated herein by reference. The system then prompts the healthcare professional with lists of medical findings such as symptoms, other physical history, physical findings, diagnosis, tests, and therapy which are listed in the database file 20. The healthcare professional simply uses a mouse or other pointing mechanisms to select a medical finding to be added to the protocol.

Once the physical findings have been selected, the healthcare professional can select the order in which the medical findings are displayed on the display screen 12. Since the medical findings are coded, the selected medical findings are automatically placed in the protocol according to how the medical findings are originally stored in the database file 20. In other words, the system knows which of the selected medical findings are symptoms, other history, physical findings, diagnosis, tests, and therapy. Thus, the healthcare professional can select the order in which the sections can be displayed on the screen.

Once the protocol has been formed, the healthcare professional can call up the desired protocol when needed for a particular patient. During the encounter, the healthcare professional can select from the lists of medical findings in the protocol those which match or most closely resemble the symptoms, history, etc. disclosed by the patient. However, before or during the encounter, the healthcare professional may use the protocol to review findings from previous encounters related to the protocol. The healthcare professional selects the medical findings by clicking, pointing, or tapping with a device to enter items on the protocol into the patient's chart. Each of these selected medical findings may be modified by a list of modifiers such as small, moderate, severe, etc. And in addition, the course of the symptoms may also be selected, i.e. improving, worsening, etc. In addition, if prescription medicines are selected and made part of the protocol, the dosage, the frequency, how the medicine is supplied, the amount to dispense, etc. may also be specified using prompted lists. In addition, medical findings not illustrated in the protocol can be entered into the patient chart using the keyboard 18.

If the selection of a medical finding is performed on the first few characters, for example, 3, of the medical finding, it is entered into the patient's chart as a positive statement of the listed finding. Thus, if the medical finding is "head trauma" and a pointer points at the first few characters of the word "head", the medical finding will be entered into the patient's chart as "head trauma". However, if the selection is made to the right of the first few characters, the finding is entered into the patient's chart as a negative response. For example, if the medical finding is "head trauma", and the pointer used to select the medical finding points at the word "trauma", the medical finding will be entered into the patient's chart as "no head trauma". When the medical findings are displayed on the screen, to the left of each medical finding a plus sign (+) may be displayed. If the pointer is pointed at the plus sign and the physical finding is selected, subsidiary findings giving more detailed information about the selected finding are displayed from which the healthcare professional may select a more detailed description to be entered into the patient chart. For example, the screen may illustrate "+ cough". If the healthcare professional clicks on the plus sign, the system will display a list of more descriptive information about the cough such as "a cough worse in the morning", a "brassy cough", etc.

FIG. 3 illustrates an example of a protocol created according to one embodiment of the present invention. The protocol is for angina and is divided into five sections: Symptoms; History; Physical Exam; Diagnoses; and Therapy. The protocol first lists a plurality of symptoms which usually occur when a person is suffering from angina. As illustrated in FIG. 3, the symptoms include among others chest pain occurrence, palpitations, difficulty breathing (dyspnea), awaking at night short of breath, and dizziness. As noted above, some of the listed symptoms as well as other medical findings in the protocol are displayed with a plus sign (+) which indicates that more detailed descriptions are available for those medical findings.

The history section lists topics which should be discussed with the patient such as a history of smoking cigarettes, medication history, physical activity, etc. The physical exam section lists various physical conditions to look for during the physical examination of the patient such as bradycardia, tachycardia, heart sounds, murmurs, and edema. In addition, a protocol for Vital Signs is also referenced which allows the healthcare professional to use a protocol within the main protocol. The diagnosis section lists history of Diabetes Mellitus and Hypertension where the symbol "H" indicates history. Finally, the protocol includes a therapy section which lists several medications which can be prescribed to combat the problems faced by the patient.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A method for creating and using a reusable medical protocol to create a patient chart which is divided into several sections, comprising the steps of:

creating said protocol by selecting various medical findings from a database containing a plurality of coded medical findings which are displayed on a display screen, wherein said coded medical findings are grouped into several sections;

selecting an order of display of said selected findings within the protocol;

displaying said protocol on a display screen;

selecting medical findings displayed in said protocol which describe a patient's situation; and, automatically placing the selected medical findings in the correct section of the patient chart based upon the code of the select ed medical findings.

2. A method according to claim 1, wherein the patient chart is divided into a symptom section, a history section, a physical findings section, a diagnosis section, a test section, and a therapy section.

3. A method according to claim 1, wherein the medical findings within said database are grouped into a symptom section, a history section, a physical findings section, a diagnosis section, a test section, and a therapy section.

4. A method according to claim 1, wherein the medical findings selected when creating the protocol can be modified to be more descriptive.

5. A method according to claim 1, wherein other protocols can be selected as part of the protocol being created.

6. A method according to claim 1, wherein a user either clicks, points, or taps a device to enter items on the protocol into the patient's chart.

7. A method according to claim 6, wherein if the selection of the medical finding is done on the first few characters of the finding, the medical finding is entered as a positive finding into the patient's chart.

8. A method according to claim 6, wherein if the selection is done to the right of the first few characters of the finding, the medical findings are entered as a negative response in the patient chart.

9. A method according to claim 6, wherein if the selection is done to the left of the first few characters of the finding, a more detailed list for the selected finding appears from which a more detailed finding may be selected and entered into the patient's chart.

10. The method of claim 1, further comprising the step of comparing the selected medical findings which describe the patient's situation with medical findings in a different medical protocol.

11. The method of claim 1, further comprising the step of comparing the selected medical findings which describe the patient's situation with medical findings in a previously displayed medical protocol.

12. A device for creating and using a reusable medical protocol to create a patient chart which is divided into several sections, comprising:

means for creating said protocol by selecting various medical findings from a database means containing a plurality of coded medical findings, wherein said coded medical findings are grouped into several different sections;

means for selecting the order of the display of said findings within the protocol;

display means for displaying the created protocol;

means for selecting medical findings displayed for said protocol which describe the patient's situation; and, means for automatically placing the selected medical findings in the correct section of the patient's chart based upon the code of the selected medical finding.

13. A device according to claim 12, wherein the patient chart is divided into a symptom section, a history section, a physical findings section, a diagnosis section, a test section, and a therapy section.

14. A device according to claim 12, wherein the medical findings within the database are grouped into a symptom section, a history section, a physical findings section, a diagnosis section, a test section, and a therapy section.

15. A device according to claim 12, wherein the medical findings selected when creating the protocol can be modified to be more descriptive.

16. A device according to claim 12, wherein other protocols can be selected as part of the protocol being created.

17. A device according to claim 12, wherein a user either clicks, points or taps a device to enter items on the protocol into the patient chart.

18. A method according to claim 17, wherein if the selection of the medical finding is done on the first few characters of the finding, the medical finding is entered as a positive finding in the patient chart.

19. A device according to claim 17, wherein if the selection is done to the right of the first few characters of the finding the medical finding is entered as a negative response in the patient chart.

20. A device according to claim 17, wherein if the selection is done to the left of the first few characters of the finding a more detailed list for the selected finding appears from which a more detailed finding may be selected and entered into the patient's chart.

21. The device of claim 12, further comprising means for comparing the selected medical findings which describe the patient's situation with medical findings in a different medical protocol.

22. The device of claim 12, further comprising means for comparing the selected medical findings which describe the patient's situation with medical findings in a previously displayed medical protocol.

* * * * *